US006829052B2

United States Patent
Naya

(10) Patent No.: US 6,829,052 B2
(45) Date of Patent: Dec. 7, 2004

(54) SENSOR DETECTING ATTENUATED TOTAL REFLECTION ANGLE BY USING SEMICONDUCTOR LASER UNIT DRIVEN WITH DRIVING CURRENT ON WHICH HIGH FREQUENCY COMPONENT IS SUPERIMPOSED

(75) Inventor: Masayuki Naya, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 202 days.

(21) Appl. No.: 10/025,699

(22) Filed: Dec. 26, 2001

(65) Prior Publication Data

US 2002/0109846 A1 Aug. 15, 2002

(30) Foreign Application Priority Data

Dec. 25, 2000 (JP) ........................................ 2000-392491

(51) Int. Cl.⁷ ............................................... G01N 21/55
(52) U.S. Cl. ........................................................ 356/445
(58) Field of Search ........................................ 356/445

(56) References Cited

U.S. PATENT DOCUMENTS 4,480,325 A * 10/1984 Aiki et al. .................. 369/122
5,875,032 A * 2/1999 Naya .......................... 356/445

FOREIGN PATENT DOCUMENTS

JP          6-167443         6/1994

OTHER PUBLICATIONS

Surface Refracto–Sensor Using Evanescent Waves Principles and Instrumentations, Takayuki Okamoto, Optical Engineering Laboratory, The Institute of Physical and Chemical Research (RIKEN) (Received Dec. 8, 1997), "Spectral Researches" / vol. 47, Nov. 1, 1998.

* cited by examiner

Primary Examiner—Richard A. Rosenberger
(74) Attorney, Agent, or Firm—Sughrue Mion, PLLC

(57) ABSTRACT

In a sensor: a thin film is formed on a face of the dielectric block and in contact with a specimen; a semiconductor laser unit as a light source emits a light beam; an optical system injects the light beam into the dielectric block so that the light beam is incident on a boundary between the dielectric block and the thin film at a plurality of incident angles which are greater than a critical angle for total reflection; and a light detecting unit detects a state of attenuated total reflection by measuring the intensity of the light beam totally reflected from the boundary. The semiconductor laser unit is driven with a driving current on which a high frequency component is superimposed.

15 Claims, 12 Drawing Sheets

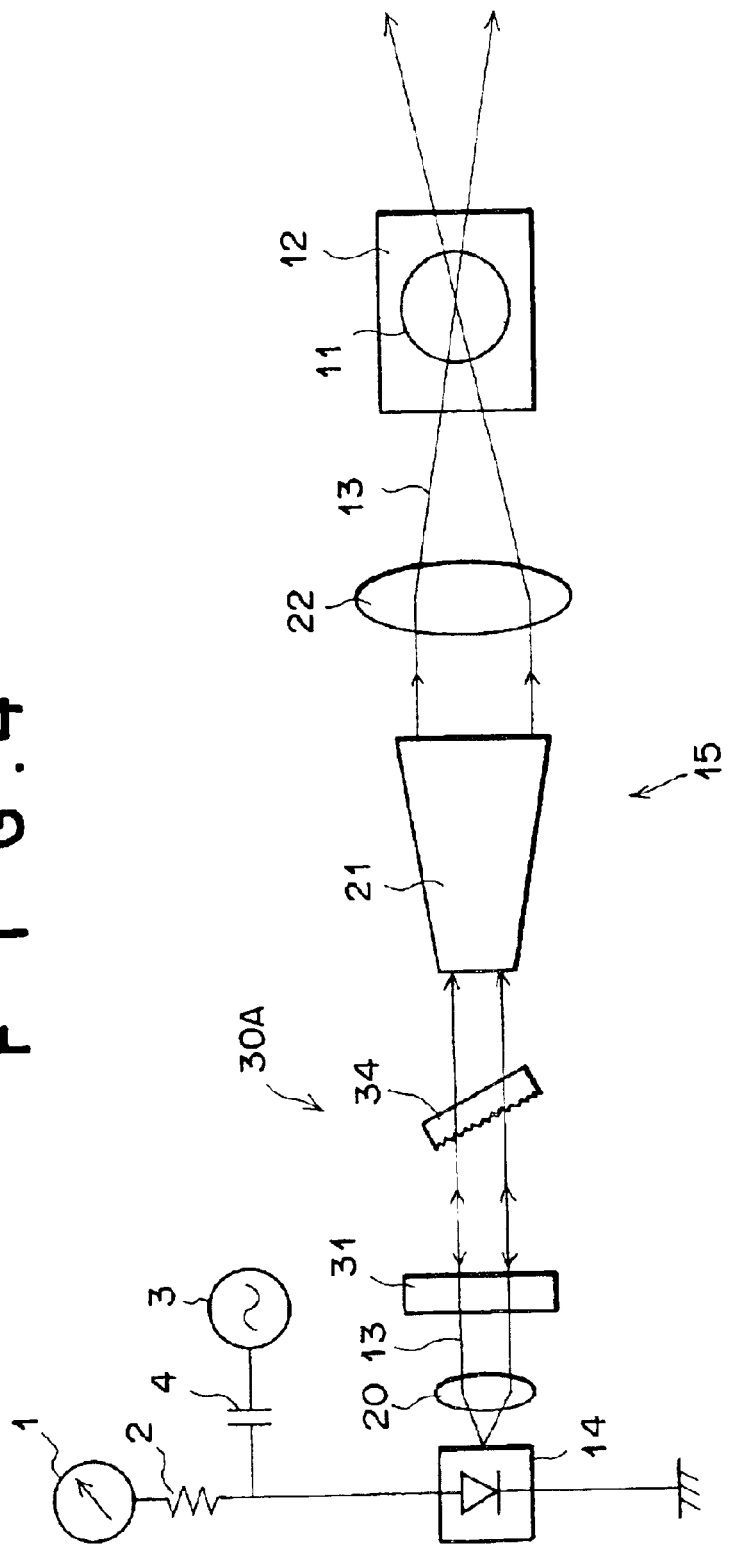

SENSOR DETECTING ATTENUATED TOTAL REFLECTION ANGLE BY USING SEMICONDUCTOR LASER UNIT DRIVEN WITH DRIVING CURRENT ON WHICH HIGH FREQUENCY COMPONENT IS SUPERIMPOSED

BACKGROUND OF THE INVENTION

1. Field of the Invention

The present invention relates to a sensor which utilizes attenuated total reflection (ATR), such as a surface plasmon sensor which enables quantitative analysis of a specific material contained in a specimen by utilizing generation of surface plasmons.

2. Description of the Related Art

In metal, free electrons move collectively to produce a compressional wave called a plasma wave. When a plasma wave generated at a surface of the metal is quantized, the plasma wave is regarded as surface plasmons.

The surface plasmons can be produced by exciting a surface of a metal by an optical wave. Conventionally, various surface plasmon sensors are proposed for performing a quantitative analysis of a material contained in a specimen by utilizing the excitation by an optical wave. In particular, surface plasmon sensors which use a system called Kretschmann's arrangement are well known (Refer to Japanese Unexamined Patent Publication No. 6(1994)-167443).

The surface plasmon sensors which use the above system basically include: a dielectric block having a form of a prism; a metal film formed on a face of the dielectric block and in contact with a specimen; a light source producing a light beam, an optical system injecting the light into the dielectric block at various incident angles which are greater than a critical angle for total reflection, and attenuated total reflection (ATR) due to a surface plasmon resonance occurs; and a light detection unit which can detect the state of the attenuated total reflection (i.e., the state of the surface plasmon resonance) by measuring the intensity of the light beam totally reflected from the above boundary.

The above various incident angles can be realized by deflecting a relatively thin light beam so that the deflected beam is incident on the boundary at desired incident angles. Alternatively, the various incident angles can be realized by letting a relatively thick light beam be incident on the boundary so that the thick light beam converges or diverges at the boundary, and therefore the converging or diverging beam contains components incident on the boundary at the various incident angles. When the relatively thin light beam is deflected, the light beam reflected at a reflection angle which varies with the deflection of the incident light beam can be detected by a small light detector which moves corresponding to the deflection of the incident light beam, or by an area sensor extending in the direction of the variation of the reflection angle. When the relatively thick light beam is incident on the boundary, the reflected light beam can be detected by an area sensor which extends in the direction of the variation of the reflection angle so that substantially all the reflected light beam can be detected.

When a light beam is incident on the metal film in the surface plasmon sensor having the above construction at a specific incident angle $\theta_{SP}$ which is greater than a critical angle for total reflection, an evanescent wave is generated, where an electric field of the evanescent wave is spread in the vicinity of the metal film in the specimen. By the evanescent wave, surface plasmons are generated at the boundary between the metal film and the specimen. When the wave number of the evanescent wave equals the wave number of the surface plasmons, i.e., these wave numbers match, the evanescent wave is resonant with the surface plasmons, and the energy of the evanescent wave is transferred to the surface plasmons. Therefore, the intensity of the light totally reflected by the boundary between the dielectric block and the metal film sharply decreases. The decrease in the intensity of the light is detected as a dark line by the light detection unit.

The above resonance occurs only when the incident light beam is a p-polarized light beam. Therefore, it is necessary to arrange the surface plasmon sensor so that the light beam is incident on the boundary as a p-polarized light beam.

When the wave number of the surface plasmon is obtained from the incident angle $\theta_{SP}$ at which the attenuated total reflection (ATR) occurs, the permittivity of the specimen can be obtained from the wave number of the surface plasmons. That is, $$K_{SP}(\omega) = \frac{\omega}{c}\sqrt{\frac{\varepsilon_m(\omega)\varepsilon_s}{\varepsilon_m(\omega)+\varepsilon_s}},$$

where the wave number of the surface plasmon is denoted by $K_{SP}$, the angular frequency of the surface plasmon is denoted by $\omega$, the velocity of light in vacuum is denoted by $c$, and permittivities of the metal and the specimen are denoted by $\varepsilon_m$ and $\varepsilon_s$, respectively.

When the permittivity $\varepsilon_s$ of the specimen is obtained, the concentration of the specific material in the specimen can be obtained based on a predetermined calibration curve or the like. Therefore, properties relating to the permittivity (i.e., the refractive index) of the specimen can be obtained by detecting the incident angle $\theta_{SP}$ at which the intensity of the reflected light decreases.

In addition, the leakage mode sensor is known as another sensor which is also utilizes the attenuated total reflection and similar to the surface plasmon sensor. For example, the leakage mode sensor disclosed in "Spectral Researches", Vol. 47, No. 1 (1998) pp. 21–23 & 26–27 includes: a dielectric block having a form of a prism; a cladding layer formed on a face of the dielectric block; an optical waveguide layer formed on the cladding layer and in contact with a specimen; a light source producing a light beam, an optical system which injects the light beam into the dielectric block at various incident angles so that the light beam is totally reflected at the boundary between the dielectric block and the cladding layer, and attenuated total reflection (ATR) due to excitation of a propagation mode in the optical waveguide layer can occur; and a light detection unit which can detect the state of the attenuated total reflection, i.e., the state of the excitation of the propagation mode, by measuring the intensity of the light beam totally reflected from the above boundary.

When the laser beam is incident through the dielectric block on the cladding layer in the above leakage mode sensor at a incident angle which is greater than the critical angle for total reflection, only a portion of light being incident on the cladding layer at a specific incident angle and having a specific wave number can propagate in the propagation mode in the optical waveguide layer. Therefore, when the propagation mode is excited, almost all portions of the incident light can enter the optical waveguide layer, i.e., the attenuated total reflection, in which the intensity of light totally reflected from the boundary sharply decreases, occurs. At this time, the wave number of the propagated light depends on the refractive index of the specimen placed on the optical waveguide layer. Therefore, it is possible to obtain the refractive index of the specimen and analyze other properties of the specimen relating to the refractive index.

Incidentally, in the conventional sensors utilizing the attenuated total reflection such as the surface plasmon sensors and leakage mode sensors, semiconductor laser devices are used as the light sources. However, in the conventional sensors using the semiconductor laser devices as the light sources and utilizing the attenuated total reflection, sometimes, the output of the light detection unit, which detects the state of the attenuated total reflection, suddenly varies, and resultantly the precision of measurement deteriorates.

SUMMARY OF THE INVENTION

An object of the present invention is to provide a sensor utilizing the attenuated total reflection, in which sudden variation in the output of a light detection unit is prevented so that high precision of measurement is achieved.

(1) According to the first aspect of the present invention, there is provided a sensor comprising: a dielectric block; a thin film formed on a face of the dielectric block and in contact with a specimen; a semiconductor laser unit as a light source which emits a light beam; a first optical system which injects the light beam into the dielectric block so that the light beam is incident on a boundary between the dielectric block and the thin film at a plurality of incident angles which are greater than a critical angle for total reflection; and a light detecting unit which detects a state of attenuated total reflection by measuring the intensity of the light beam totally reflected from the boundary. In the sensor, the semiconductor laser unit is driven with a driving current on which a high frequency component is superimposed.

(2) According to the second aspect of the present invention, there is provided a sensor comprising: a dielectric block; a metal film formed on a face of the dielectric block and in contact with a specimen; a semiconductor laser unit as a light source which emits a light beam; a first optical system which injects the light beam into the dielectric block so that the light beam is incident on a boundary between the dielectric block and the metal film at a plurality of incident angles which are greater than a critical angle for total reflection; and a light detecting unit which detects a state of attenuated total reflection due to surface plasmon resonance by measuring the intensity of the light beam totally reflected from the boundary. In the sensor, the semiconductor laser unit is driven with a driving current on which a high frequency component is superimposed.

(3) According to the third aspect of the present invention, there is provided a sensor comprising: a dielectric block; a cladding layer formed on a face of the dielectric block; an optical waveguide layer formed on the cladding layer and in contact with a specimen; a semiconductor laser unit as a light source which emits a light beam; a first optical system which injects the light beam into the dielectric block so that the light beam is incident on a boundary between the dielectric block and the cladding layer at a plurality of incident angles which are greater than a critical angle for total reflection; and a light detecting unit which detects a state of attenuated total reflection due to excitation of a propagation mode in the optical waveguide layer, by measuring the intensity of the light beam totally reflected from the boundary. In the sensor, the semiconductor laser unit is driven with a driving current on which a high frequency component is superimposed.

(4) Preferably, the sensor according to each of the first to third aspects of the present invention may also have one or any possible combination of the following additional features (a) to (g).

(a) The semiconductor laser unit may comprise a stabilization unit for stabilizing an oscillation wavelength.

(b) The above stabilization unit may comprise a second optical system which feeds back to the semiconductor laser unit a portion of the light beam emitted from the semiconductor laser unit, and a wavelength selection unit which selects a wavelength of the portion of the light beam.

(c) In the case where the wavelength selection unit is realized by using a bulk grating, the second optical system can be formed as follows.

(i) The second optical system may comprise an optical splitting unit and a reflective grating. The optical splitting unit is arranged in an optical path of the light beam emitted from the light source toward the dielectric block, and splits off a portion of the light beam from the optical path. The reflective grating functions as the wavelength selection unit, and reflects a component of the split-off portion of the light beam having the selected wavelength so that the reflected component of the split-off portion of the light beam retraces the path of the split-off portion of the light beam, and is fed back to the light source.

(ii) The second optical system and the wavelength selection unit may be realized by a partially reflective grating which is arranged in an optical path of the light beam emitted from the light source toward the dielectric block, and partially reflects a portion of the light beam having the selected wavelength so that the partially reflected portion of the light beam is fed back to the light source.

(iii) The second optical system and the wavelength selection unit may be realized by a reflective grating which reflects a portion of backward emission light having the selected wavelength so that the reflected portion of the backward emission light is fed back to the light source, where the backward emission light is emitted from the semiconductor laser unit in the direction opposite to the direction of the light beam incident on the dielectric block.

(d) In the case where the wavelength selection unit is realized by using a narrow-band-pass filter, the second optical system can be formed as follows.

(i) The second optical system may comprise an optical splitting unit and a mirror. The optical splitting unit is arranged in an optical path of the light beam emitted from the light source toward the dielectric block, and splits off a portion of the light beam from the optical path. The mirror reflects the split-off portion of the light beam so that the reflected portion of the light beam retraces the path of the split-off portion of the light beam, and is fed back to the light source. The narrow-band-pass filter as the wavelength selection unit is arranged between the optical splitting unit and the mirror so that only a component of the split-off portion of the light beam having a wavelength selected by the narrow-band-pass filter is fed back to the light source.

(ii) The second optical system may be realized by a half mirror, which is arranged in an optical path of the light beam emitted from the light source toward the dielectric block, and partially reflects the light beam, and feeds back a portion of the light beam to the light source. The narrow-band-pass filter is arranged in the optical path between the light source and the half mirror so that only a portion of the light beam having a wavelength selected by the narrow-band-pass filter is fed back to the light source.

(iii) The second optical system may be realized by a mirror, which reflects a portion of backward emission light, and feeds back the backward emission light to the light source, where the backward emission light is emitted from the semiconductor laser unit in the direction opposite to the direction of the light beam incident on the dielectric block. The narrow-band-pass filter is arranged in the optical path between the light source and the mirror so that only a portion of the backward emission light having a wavelength selected by the narrow-band-pass filter is fed back to the light source.

(e) The wavelength selection unit may be realized by using a fiber grating, which diffracts and reflects a light beam. The fiber grating is an optical fiber having a core in which a plurality of refractive-index varied portions are formed in the core at regular intervals. In this case, the second optical system can be formed as follows.

(i) The second optical system may comprise an optical splitting unit and the fiber grating which realizes the wavelength selection unit. The optical splitting unit is arranged in an optical path of the light beam emitted from the light source toward the dielectric block, and splits off a portion of the light beam from the optical path. The fiber grating diffracts and reflects a component of the split-off portion of the light beam having the selected wavelength so that the reflected component of the split-off portion of the light beam retraces the path of the split-off portion of the light beam, and is fed back to the light source.

(ii) The second optical system and the wavelength selection unit may be realized by a partially reflective fiber grating which is arranged in an optical path of the light beam emitted from the light source toward the dielectric block, and partially reflects a portion of the light beam having the selected wavelength so that the partially reflected portion of the light beam is fed back to the light source.

(iii) The second optical system and the wavelength selection unit may be realized by the fiber grating. In this case, the fiber grating reflects a portion of backward emission light having the selected wavelength so that the reflected portion of the backward emission light is fed back to the light source, where the backward emission light is emitted from the semiconductor laser unit in the direction opposite to the direction of the light beam incident on the dielectric block.

(iv) Note that in the case that the oscillation wavelength is stabilized by optical feedback, it is preferable that the frequency of the high-frequency component superimposed on the semiconductor laser is within the range of 200 MHz–1000 MHz.

(f) It is possible to use as the light source a semiconductor laser unit in which a wavelength stabilization unit is built in, such as a DFB (distributed feedback) laser or DBR (distributed Bragg reflector) laser. In this case, the oscillation wavelength can be stabilized without providing the second optical system for optical feedback.

(g) Alternatively, it is possible to stabilize the oscillation wavelength by electrically and finely controlling the temperature and the driving current of the semiconductor laser unit.

(5) The present invention has the following advantages.

(a) As a result of the inventor's investigation, the inventor has recognized that mode hopping in the semiconductor laser unit causes the aforementioned sudden variations in the output of the light detection unit which detects the state of the attenuated total reflection, and deterioration of the precision in the measurement in the case where the semiconductor laser unit is used as a light source in a sensor utilizing the attenuated total reflection.

Based on the above recognition, the high-frequency current RF is superimposed on the driving current of the semiconductor laser unit so that the oscillation mode of the semiconductor laser unit becomes multiple modes. When the semiconductor laser unit oscillates in multiple modes, variations in the output of the light detection unit caused by the difference in the oscillation mode are averaged. Therefore, high precision in the measurement can be achieved.

(b) When the oscillation wavelength of the semiconductor laser unit in the sensor utilizing the attenuated total reflection is stabilized by the wavelength stabilization unit, it is possible to prevent production of noise or drift in the output of the light detection unit caused by variations in the oscillation wavelength, and improve precision in measurement.

Further, in the case that the oscillation frequency is stabilized by optical feedback, it became evident that by setting the frequency of the high-frequency component to be superimposed on the semiconductor laser within a range of 200 MHz–1000 MHz, the oscillation wavelength (central wavelength) of the semiconductor was stabilized and maintained at a predetermined value. Therefore, by setting the frequency of the high-frequency component within the range described above, a stable measurement signal can be obtained, and particularly high accuracy in measurement becomes possible.

DESCRIPTION OF THE DRAWINGS

FIG. 4 is a plan view of a surface plasmon sensor as a second embodiment of the present invention.

DESCRIPTION OF PREFERRED EMBODIMENTS

Embodiments of the present invention are explained in detail below with reference to drawings.

First Embodiment

Figure 1:
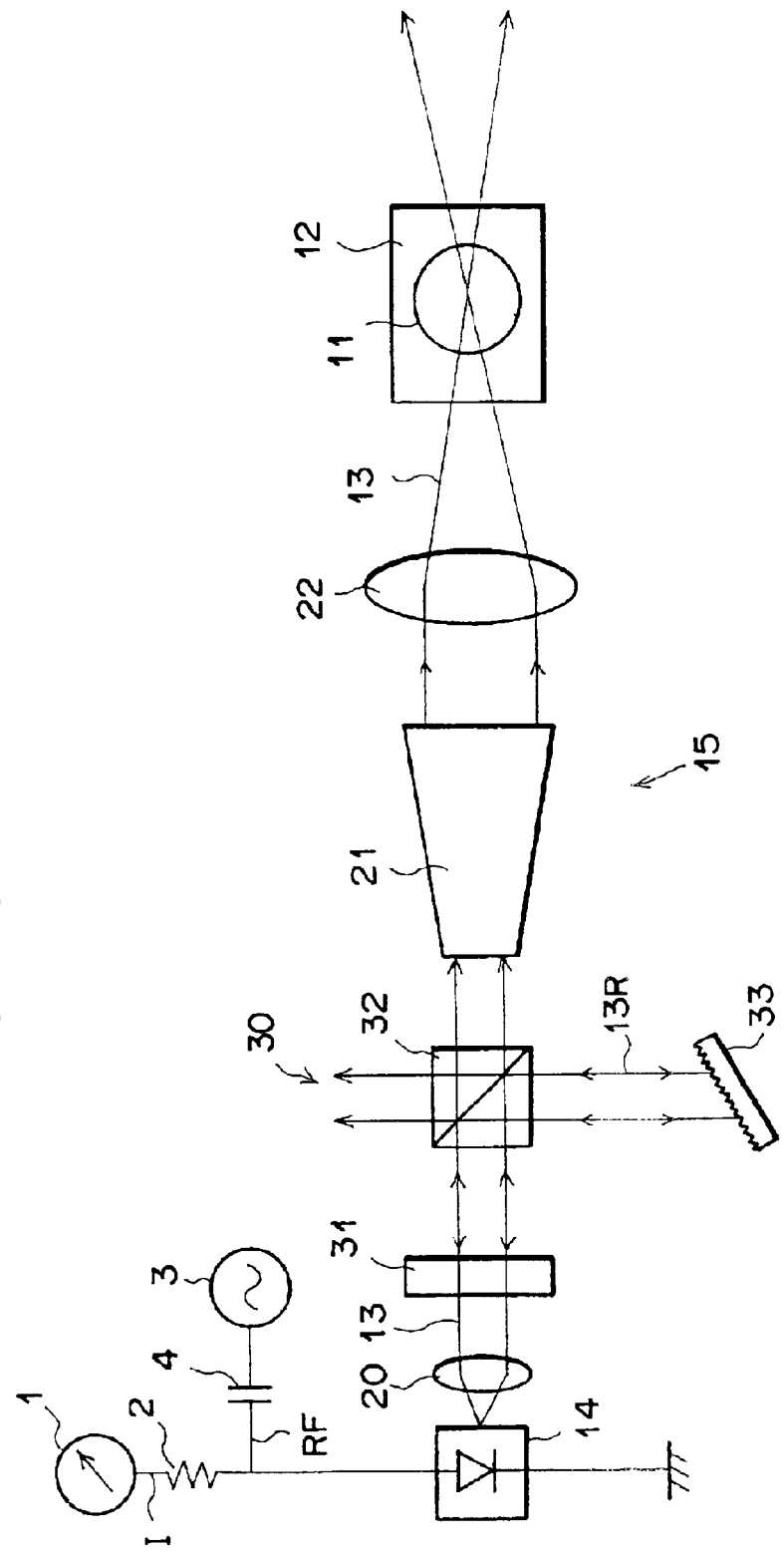
FIG. 1 is a plan view of a surface plasmon sensor as a first embodiment of the present invention.
Figure 2:
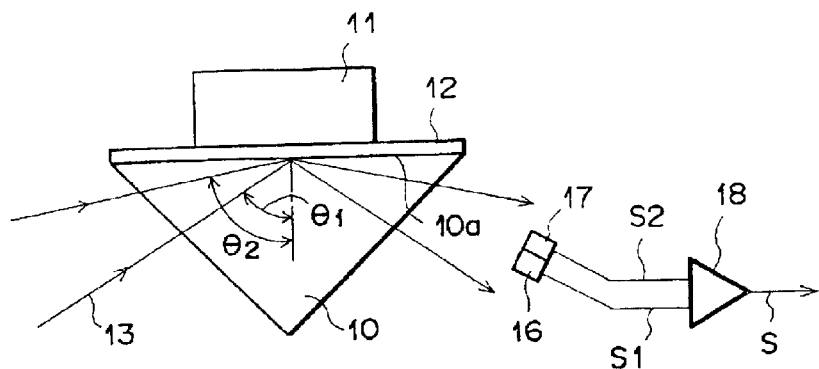
FIG. 2 is a side view of a portion of the surface plasmon sensor of FIG. 1.

FIG. 1 is a plan view of a surface plasmon sensor as a first embodiment of the present invention, and FIG. 2 is a side view of a surface plasmon detection portion of the surface plasmon sensor of FIG. 1.

As illustrated in FIGS. 1 and 2, the surface plasmon sensor as the first embodiment of the present invention comprises a prism 10, a metal film 12, a semiconductor laser unit 14, an optical system 15, first and second light detection units 16 and 17, a comparator 18, and a wavelength stabilization unit 30.

The prism 10 has a form of a wedge, the main axis of which is in the vertical direction in the plane of FIG. 1 and perpendicular to the plane of FIG. 2. The metal film 12 is formed on a face of the prism 10, and a specimen 11 is placed on the metal film 12. Thus, the metal film 12 is in contact with the specimen 11. For example, the metal film 12 is made of gold or silver. The semiconductor laser unit 14 emits a light beam (laser beam) 13 which has a center wavelength of, for example, 685 nm. The optical system 15 leads to the prism 10 the laser beam 13 emitted from the semiconductor laser unit 14, and injects the laser beam 13 into the prism 10 so that the laser beam 13 can be incident on the boundary 10a between the prism 10 and the metal film 12 at a plurality of incident angles. The first and second light detection units 16 and 17 are connected to the comparator 18, and each detects the intensity of a portion of the laser beam 13 which is totally reflected from the boundary 10a.

A predetermined DC current I is supplied from a DC power supply 1 to he semiconductor laser unit 14 through a resistor 2. In addition, a high-frequency current RF is supplied from a high-frequency power supply 3 through an AC coupling capacitance 4, and superimposed on the DC current I. Thus, the semiconductor laser unit 14 is driven with a driving current on which a high-frequency current RF is superimposed. The frequency of the high-frequency current RF is, for example, about 350 MHz.

The optical system 15 comprises a collimator lens 20, a beam expander 21, and a condenser lens 22. The collimator lens 20 collimates the laser beam 13, which is emitted from the semiconductor laser unit 14 in the form of a divergent light beam. The beam expander 21 increases the diameter of the collimated laser beam 13. The condenser lens 22 converges the collimated laser beam 13 which is expanded by the beam expander 21, so that the laser beam 13 converges on the boundary 10a.

The laser beam 13 is incident on the boundary 10a as a p-polarized light beam. The semiconductor laser unit 14 may be arranged in advance so that the polarization direction of the laser beam 13 emitted from the semiconductor laser unit 14 becomes a p-polarized light beam at the boundary 10a. Alternatively, the polarization direction of the laser beam 13 may be controlled by using a wavelength plate or a polarization plate.

Since the laser beam 13 is converged by the condenser lens 22, the laser beam 13 incident on the boundary 10a contains components which are incident on the boundary 10a at various incident angles θ between minimum and maximum incident angles $θ_1$ and $θ_2$ as illustrated in FIG. 2, where the various incident angles are greater than a critical angle for total reflection. That is, the laser beam 13 is totally reflected at the boundary 10a, and the totally reflected laser beam 13 also contains components which are reflected at the boundary 10a at various reflection angles.

The first and second light detection units 16 and 17 can be realized by, for example, a half-split photodiode. The first light detection unit 16 is arranged to detect an amount of light components of the laser beam 13 totally reflected from the boundary 10a at reflection angles in a first reflection angle range, and the second light detection unit 17 is arranged to detect an amount of other light components of the laser beam 13 totally reflected from the boundary 10a at reflection angles in a second reflection angle range, where the first reflection angle range is located on the lower angle side of the second reflection angle range.

Analysis of the specimen 11 is made by using the above surface plasmon sensor as follows.

The specimen 11 to be analyzed is held in a predetermined position in contact with the metal film 12. The laser beam 13 converged by the condenser lens 22 is incident on the metal film 12. Then, the laser beam 13 totally reflected from the boundary 10a between the metal film 12 and the prism 10 is detected by the first and second light detection units 16 and 17 as described above.

In response to the detection of the totally reflected laser beam 13, the first light detection unit 16 outputs a light-amount detection signal S1, and the second light detection unit 17 outputs a light-amount detection signal S2. The light-amount detection signals S1 and S2 are input into the comparator 18, which outputs a difference signal S indicating the difference between the light-amount detection signals S1 and S2.

Figure 3A:
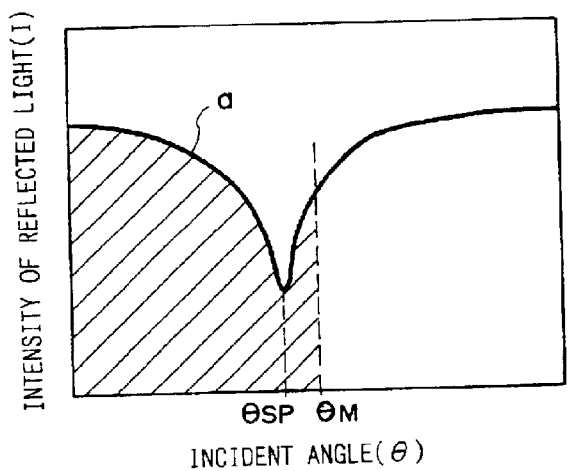
FIGS. 3A and 3B are diagrams each illustrating an example of a relationship between an incident angle $\theta$ and an intensity of light detected by an optical detection unit in a surface plasmon sensor.
Figure 3B:
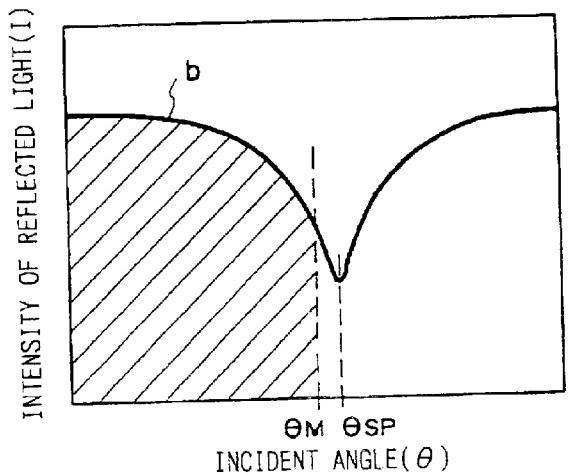

When light is incident on the boundary 10a at a specific incident angle $θ_{SP}$, surface plasmons are excited at the boundary 10a between the metal film 12 and the specimen 11, and therefore the intensity of the reflected light sharply decreases. That is, the relationship between the incident angle θ and the intensity I of the reflected light is expressed by, for example, the curve a or b illustrated in FIGS. 3A and 3B. Therefore, it is possible to make a quantitative analysis of a specific material contained in the specimen 11 based on the curve indicating the relationship between the incident angle θ and the intensity I of the reflected light.

For example, when the aforementioned first and second reflection angle ranges abut each other at a boundary angle $θ_M$, i.e., the upper limit of the first reflection angle range coincides with the lower limit of the second reflection angle range, the first light detection unit 16 detects an amount of a portion of the light reflected at reflection angles smaller than the boundary angle $θ_M$, and the second light detection unit 17 detects an amount of another portion of the light reflected at reflection angles greater than the boundary angle $θ_M$. In each of FIGS. 3A and 3B, the amount of the light reflected at the reflection angles smaller than the boundary angle $θ_M$ is illustrated as a hatched area, and the amount of the light reflected at the reflection angles greater than the boundary angle $\theta_M$ is illustrated as a non-hatched area. The first light detection unit 16 detects a greater amount of light in the case of FIG. 3B than in the case of FIG. 3A. On the other hand, the second light detection unit 17 detects a greater amount of light in the case of FIG. 3A than in the case of FIG. 3B. That is, a difference between the amounts of light detected by the first and second light detection units 16 and 17 corresponds to the relationship between the incident angle $\theta$ and the intensity I of the reflected light.

Therefore, when a calibration curve for each specimen is obtained in advance for reference, it is possible to estimate the specific incident angle $\theta_{SP}$ corresponding to the attenuated total reflection (ATR) for the specimen 11 and a curve indicating a relationship between the incident angle $\theta$ and the intensity I of the reflected light, based on the output of the comparator 18, which indicates the difference between the amounts of light detected by the first and second light detection units 16 and 17. That is, the quantitative analysis of a specific material in the specimen 11 is enabled.

Alternatively, even when the aforementioned first and second reflection angle ranges do not abut each other, the difference between the amounts of light detected by the first and second light detection units 16 and 17 also corresponds to the relationship between the incident angle $\theta$ and the intensity I of the reflected light, and it is therefore possible to make a quantitative analysis of a specific material in the specimen 11 in a similar manner.

In addition, when a sensing medium which can be bound to a specific material contained in a specimen (e.g., a liquid specimen) is fixed onto the metal film 12, and the specimen is placed in contact with the sensing medium, the refractive index of the sensing medium varies with the state of binding of the sensing medium to the specific material. Therefore, the variations in the state of binding can be investigated by continuously monitoring the difference signal S, which is output from the comparator 18. That is, in this case, both of the liquid specimen and the sensing medium function as a specimen in the surface plasmon sensor. A typical example of a combination of a specific material and a sensing medium is an antigen and an antibody.

Next, the wavelength stabilization unit 30 is explained.

As illustrated in FIG. 1, the wavelength stabilization unit 30 is arranged between the collimator lens 20 and the beam expander 21, and comprises a half-wavelength plate 31, a beam splitter 32, and a reflective grating 33. The half-wavelength plate 31 controls the polarization of the laser beam 13. The beam splitter 32 partially reflects the laser beam 13 which has passed through the half-wavelength plate 31, so as to split off a portion 13R of the laser beam 13 from the optical path toward the dielectric block 10. The reflective grating 33 is arranged so that the portion 13R of the laser beam 13 split off by the beam splitter 32 is incident on the reflective grating 33.

A component of the portion 13R of the laser beam 13 having (a very narrow spectrum including) a wavelength selected by the reflective grating 33 is returned to the beam splitter 32. Then, the component of the portion 13R of the laser beam 13 having the selected wavelength is fed back to the semiconductor laser unit 14 through the beam splitter 32 and the half-wavelength plate 31. That is, an external resonator is formed between a backward end facet of the semiconductor laser unit 14 and the reflective grating 33. Thus, the oscillation wavelength of the semiconductor laser unit 14 is locked at the wavelength selected by the reflective grating 33.

When the oscillation wavelength of the semiconductor laser unit 14 is stabilized as above, it is possible to prevent production of noise in the difference signal S due to variations in the oscillation wavelength, and achieve high precision in measurement for specimen analysis.

Further, since the high-frequency current RF is superimposed on the driving current of the semiconductor laser unit 14, the oscillation mode of the semiconductor laser unit 14 becomes multiple modes. When the semiconductor laser unit 14 oscillates in multiple modes, variations in the difference signal S due to the difference in the oscillation mode are averaged. Since the averaged difference signal S does not vary suddenly, high precision in the measurement can be achieved.

Second Embodiment

FIG. 4 is a plan view of a surface plasmon sensor as a second embodiment of the present invention. In FIG. 4, elements having the same functions as the elements in the surface plasmon sensor of FIG. 1 bear the same reference numerals as FIG. 1, respectively. The surface plasmon sensor as the second embodiment is different from the surface plasmon sensor as the first embodiment in only the wavelength stabilization unit. Therefore, only the differences from the first embodiment are explained below.

The wavelength stabilization unit 30A in the surface plasmon sensor of FIG. 4 is realized by a partially reflective grating 34, which also has a function of a wavelength selection unit. The partially reflective grating 34 is arranged in the optical path of the laser beam 13 between the semiconductor laser unit 14 and the prism 10, and reflects a portion of the laser beam 13 which has a selected wavelength. The portion of the laser beam 13 reflected by the partially reflective grating 34 is fed back to the semiconductor laser unit 14. Thus, the oscillation wavelength of the semiconductor laser unit 14 is locked at the selected wavelength.

In addition, the high-frequency current RF is superimposed on the driving current of the semiconductor laser unit 14 in the same manner to the first embodiment. Therefore, the surface plasmon sensor as the second embodiment has the same advantages as the first embodiment.

Third Embodiment

Figure 5:
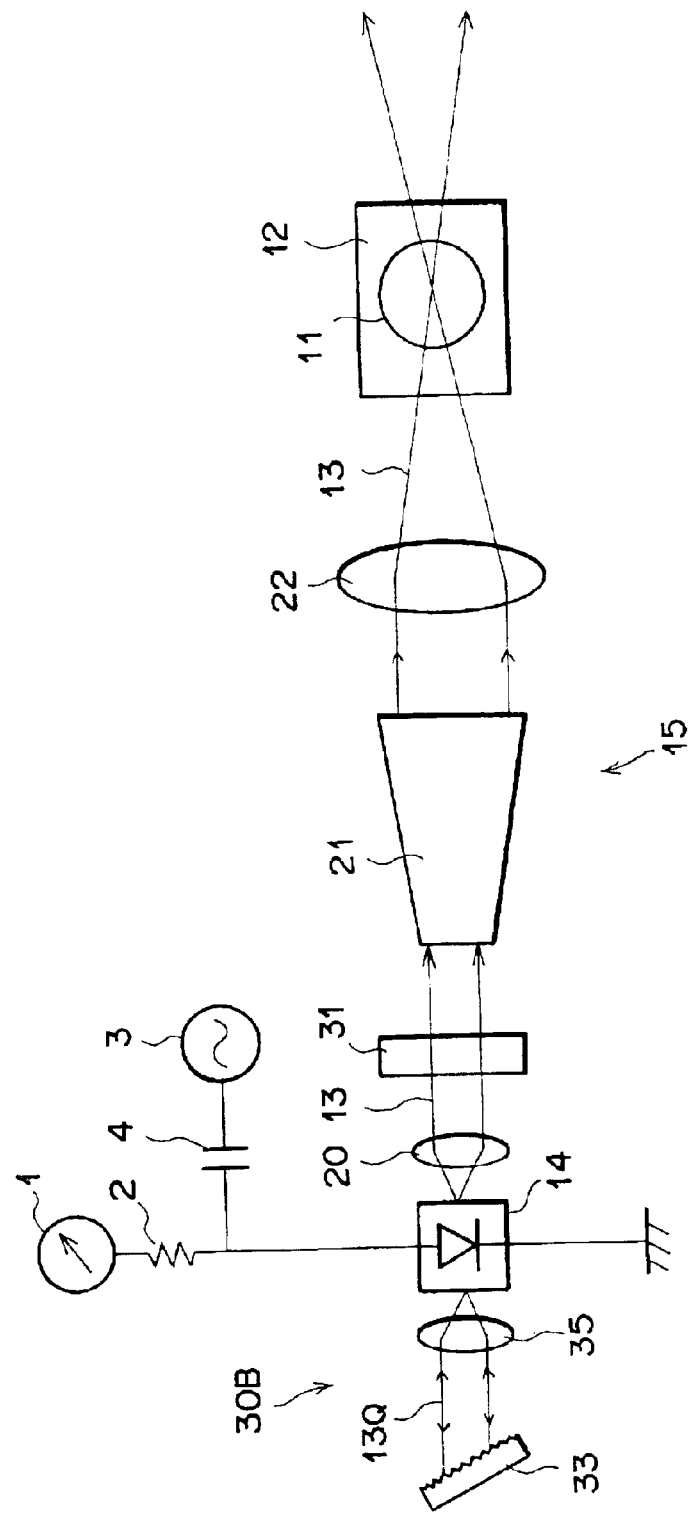
FIG. 5 is a plan view of a surface plasmon sensor as a third embodiment of the present invention.

FIG. 5 is a plan view of a surface plasmon sensor as a third embodiment of the present invention. In FIG. 5, elements having the same functions as the elements in the surface plasmon sensor of FIG. 1 bear the same reference numerals as FIG. 1, respectively. The surface plasmon sensor as the third embodiment is different from the surface plasmon sensor as the first embodiment in only the wavelength stabilization unit. Therefore, only the differences from the first embodiment are explained below.

The wavelength stabilization unit 30B in the surface plasmon sensor of FIG. 5 comprises a reflective grating 33 and a collimator lens 35. The reflective grating 33 and the collimator lens 35 constitute an optical system for optical feedback. In addition, the reflective grating 33 has a function of selecting a wavelength.

Thus, backward emission light 13Q, which is emitted from the backward side of the semiconductor laser element 14, is collimated by the collimator lens 35, and the collimated backward emission light 13Q is incident on the reflective grating 33. A wavelength of the backward emission light 13Q is selected by the reflective grating 33, and therefore a portion of the backward emission light 13Q having the selected wavelength is fed back to the semiconductor laser unit 14. Thus, the oscillation wavelength of the semiconductor laser unit 14 is locked at the selected wavelength.

Fourth Embodiment

Figure 6:
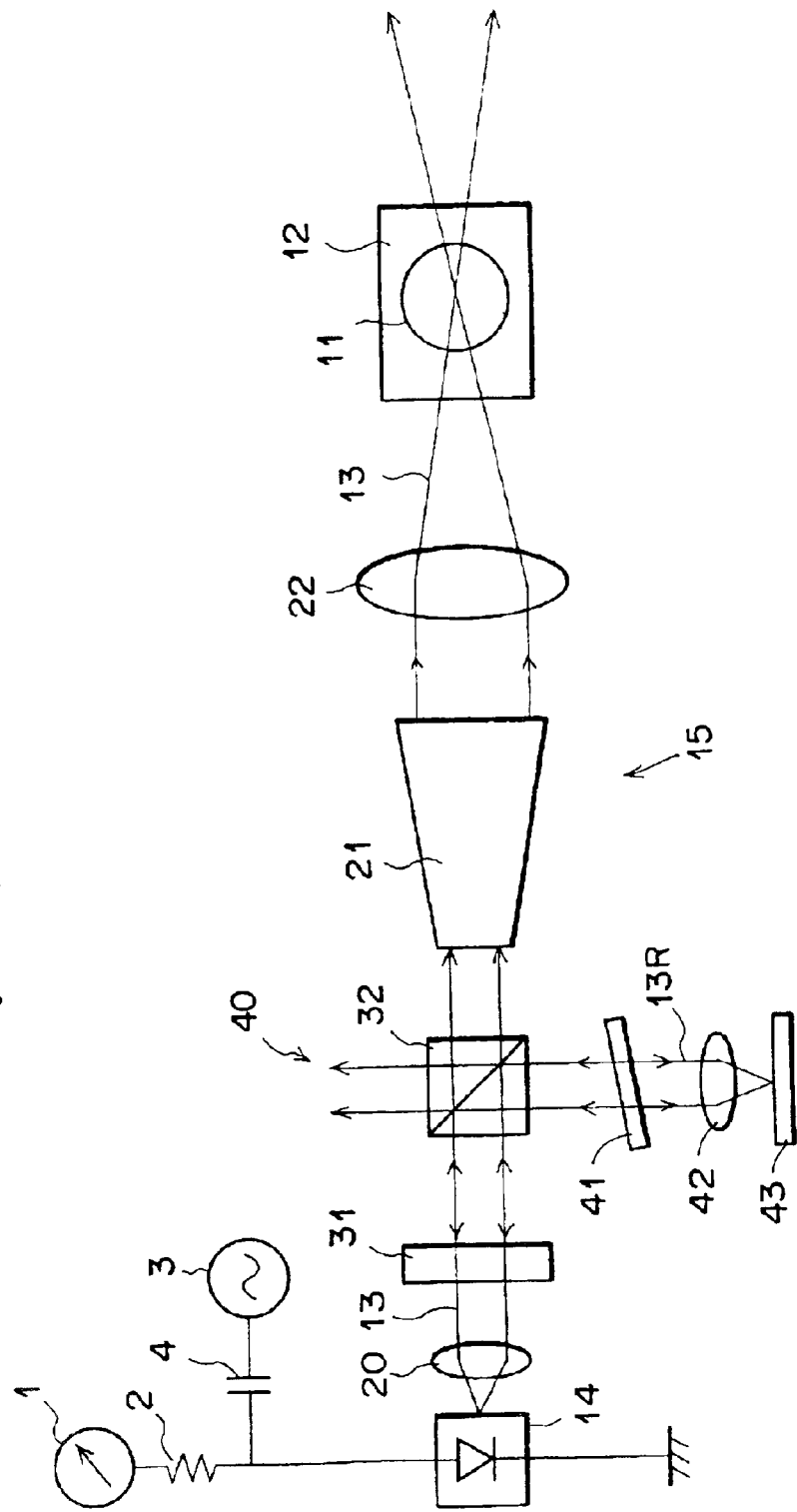
FIG. 6 is a plan view of a surface plasmon sensor as a fourth embodiment of the present invention.

FIG. 6 is a plan view of a surface plasmon sensor as a fourth embodiment of the present invention. In FIG. 6, elements having the same functions as the elements in the surface plasmon sensor of FIG. 1 bear the same reference numerals as FIG. 1, respectively. The surface plasmon sensor as the fourth embodiment is different from the surface plasmon sensor as the first embodiment in only the wavelength stabilization unit. Therefore, only the differences from the first embodiment are explained below.

The wavelength stabilization unit 40 in the surface plasmon sensor of FIG. 6 comprises a beam splitter 32, a narrow-band-pass filter 41, a condenser lens 42, and a mirror 43.

The beam splitter 32 partially reflects the laser beam 13 which has passed through the half-wavelength plate 31, so as to split off a portion 13R of the laser beam 13 from the optical path toward the prism 10. The narrow-band-pass filter 41 is arranged so that the portion 13R of the laser beam 13 split off by the beam splitter 32 is incident on the narrow-band-pass filter 41. The condenser lens 42 converges a component of the portion 13R of the laser beam 13 which has passed through the narrow-band-pass filter 41. The mirror 43 is arranged at such a position that the component of the portion 13R of the laser beam 13 which has passed through the narrow-band-pass filter 41 converges on the reflection surface of the mirror 43.

In the wavelength stabilization unit 40, only a component of the portion 13R of the laser beam 13 having a wavelength selected by the narrow-band-pass filter 41 passes through the narrow-band-pass filter 41. Then, the component of the portion 13R of the laser beam 13 having the selected wavelength is converged by the condenser lens 42, and incident on the mirror 43. The component of the portion 13R of the laser beam 13 having the selected wavelength is reflected by the mirror 43, and retraces the optical path of the light beam incident on the mirror 43. That is, the component of the portion 13R of the laser beam 13 having the selected wavelength is fed back to the semiconductor laser unit 14 through the condenser lens 42, the narrow-band-pass filter 41, the beam splitter 32, the half-wavelength plate 31, and collimator lens 20. Therefore, the oscillation wavelength of the semiconductor laser unit 14 is locked at the wavelength selected by the narrow-band-pass filter 41, and high precision is achieved in measurement.

Alternatively, a half mirror may be used instead of the beam splitter 32.

With regard to the present embodiment, the frequency of the high frequency current RF that is superimposed on the drive current of the semiconductor laser 14 by the high-frequency power supply circuit 3 is 350 MHz, which falls within the aforementioned range of 200 MHz–1000 MHz. It has been confirmed that by setting the frequency of the high-frequency current RF to this value, the light-amount detection signals S1, S2 respectively output by the optical detection means 16, 17 illustrated in FIG. 2 are stabilized. In turn, the differential signal S was also stabilized, and a particularly high accuracy in measurement became possible.

Fifth Embodiment

Figure 7:
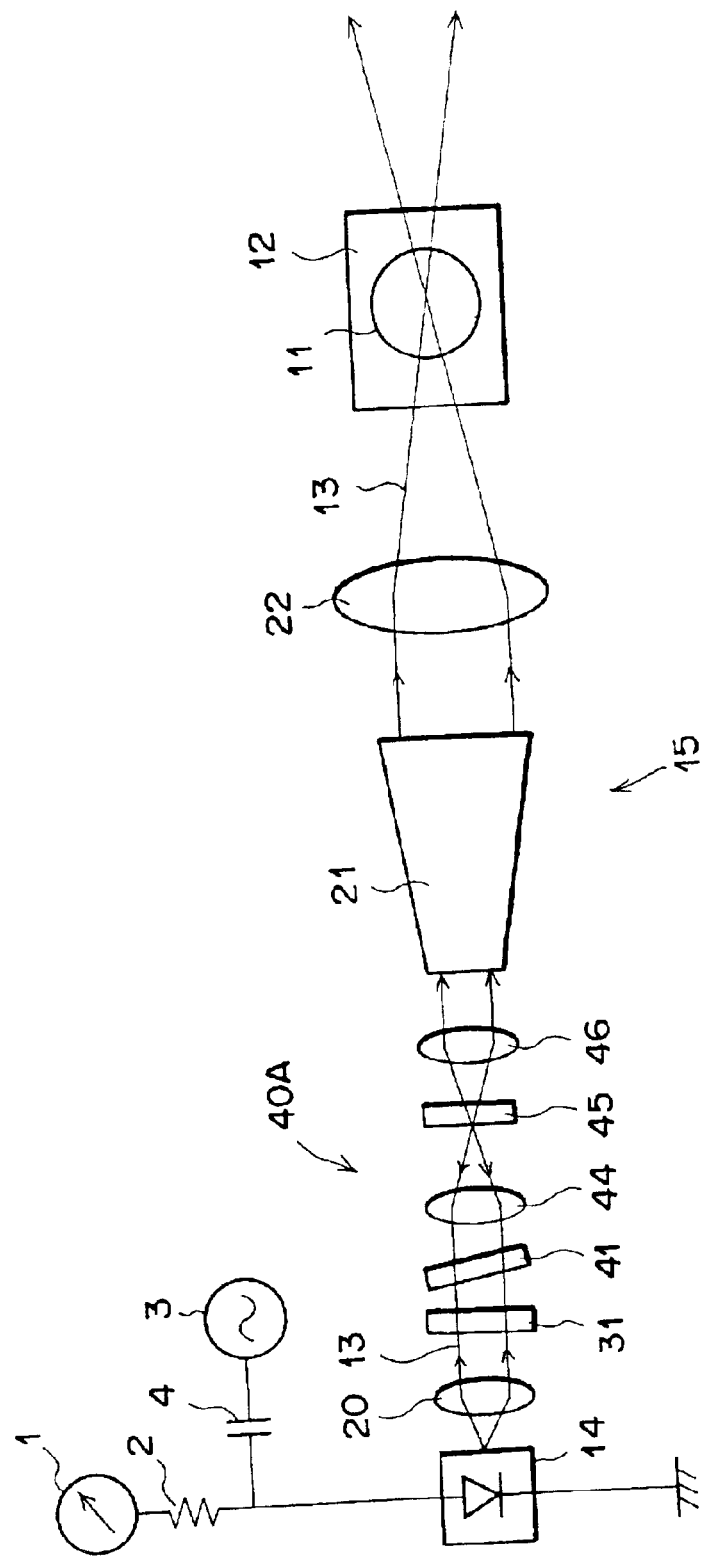
FIG. 7 is a plan view of a surface plasmon sensor as a fifth embodiment of the present invention.

FIG. 7 is a plan view of a surface plasmon sensor as a fifth embodiment of the present invention. In FIG. 7, elements having the same functions as the elements in the surface plasmon sensor of FIG. 6 bear the same reference numerals as FIG. 6, respectively. The surface plasmon sensor as the fifth embodiment is different from the surface plasmon sensor as the fourth embodiment in only the wavelength stabilization unit. Therefore, only the differences from the fourth embodiment are explained below.

The wavelength stabilization unit 40A in the surface plasmon sensor of FIG. 7 comprises a narrow-band-pass filter 41, a condenser lens 44, a half mirror 45, and a collimator lens 46, which are arranged in this order in the optical path of the laser beam 13 between the semiconductor laser unit 14 and the prism 10. The condenser lens 44 and the half mirror 45 constitute an optical system for optical feedback.

In the wavelength stabilizing unit 40A, a portion of the laser beam 13 having a wavelength selected by the narrow-band-pass filter 41 passes through the narrow-band-pass filter 41, converged by the condenser lens 44, and incident on the half mirror 45. The above portion of the laser beam 13 having the selected wavelength is reflected by the half mirror 45, and fed back to the semiconductor laser unit 14, where the half mirror 45 is arranged at such a position that the above portion of the laser beam 13 having the selected wavelength converges on the reflection surface of the half mirror 45.

Therefore, the oscillation wavelength of the semiconductor laser unit 14 is locked at the wavelength selected by the narrow-band-pass filter 41, and high precision is achieved in measurement.

Sixth Embodiment

Figure 8:
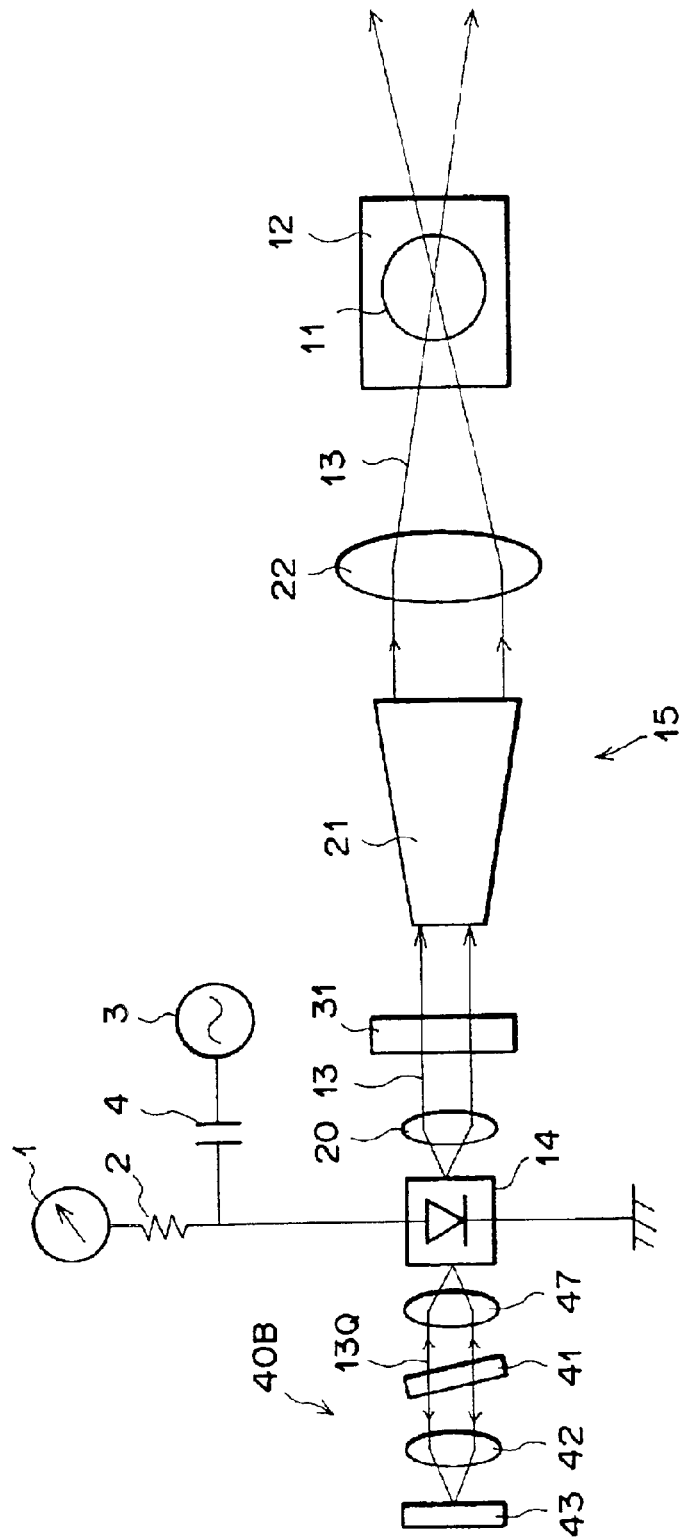
FIG. 8 is a plan view of a surface plasmon sensor as a sixth embodiment of the present invention.

FIG. 8 is a plan view of a surface plasmon sensor as a sixth embodiment of the present invention. In FIG. 8, elements having the same functions as the elements in the surface plasmon sensor of FIG. 6 bear the same reference numerals as FIG. 6, respectively. The surface plasmon sensor as the sixth embodiment is different from the surface plasmon sensor as the fourth embodiment in only the wavelength stabilization unit. Therefore, only the differences from the fourth embodiment are explained below.

The wavelength stabilization unit 40B in the surface plasmon sensor of FIG. 8 comprises a narrow-band-pass filter 41, a condenser lens 42, a mirror 43, and a collimator lens 47.

The collimator lens 47 collimates backward emission light 13Q which is emitted from the backward side of the semiconductor laser element 14. The narrow-band-pass filter 41 is arranged in the optical path of the collimated backward emission light 13Q. The condenser lens 42 converges the collimated backward emission light 13Q. The mirror 43 is arranged at such a position that the collimated backward emission light 13Q converges on the reflection surface of the mirror 43. The condenser lens 42 and the mirror 43 constitute an optical system for optical feedback, and the narrow-band-pass filter 41 has a function of selecting a wavelength.

In the wavelength stabilizing unit 40B, backward emission light 13Q, which is emitted from the backward side of the semiconductor laser element 14, is collimated by the collimator lens 47, and a portion of the collimated backward emission light 13Q having a wavelength selected by the narrow-band-pass filter 41 passes through the narrow-band-pass filter 41, converged by the condenser lens 42, and reflected by the mirror 43. The reflected portion of the backward emission light 13Q retraces the optical path of the portion of the backward emission light 13Q incident on the mirror 43. That is, the wavelength-selected and reflected portion of the backward emission light 13Q is fed back to the semiconductor laser unit 14 through the condenser lens 42, the narrow-band-pass filter 41, and the collimator lens 47. Therefore, the oscillation wavelength of the semiconductor laser unit 14 is locked at the wavelength selected by the narrow-band-pass filter 41.

Seventh Embodiment

Figure 9:
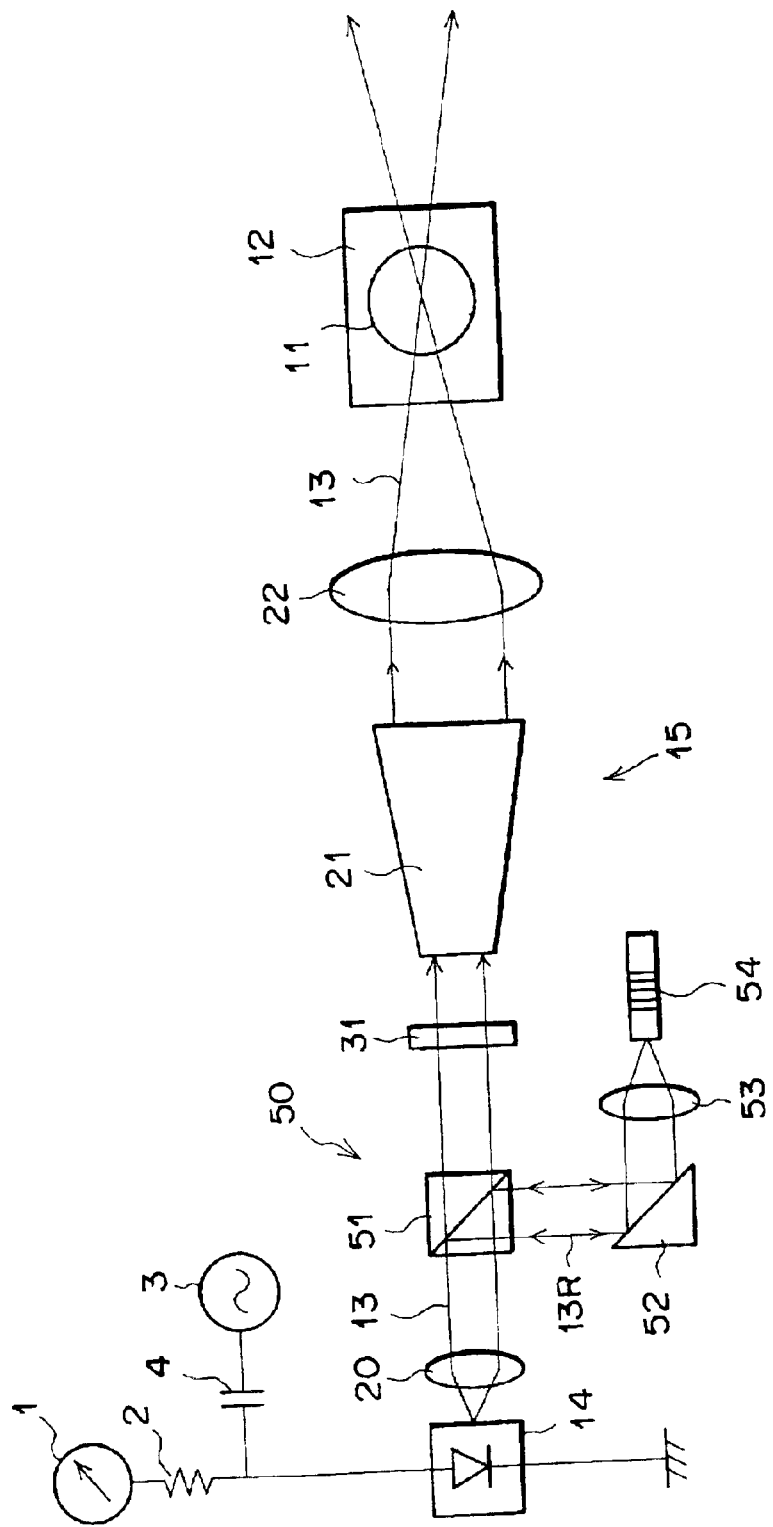
FIG. 9 is a plan view of a surface plasmon sensor as a seventh embodiment of the present invention.

FIG. 9 is a plan view of a surface plasmon sensor as a seventh embodiment of the present invention. In FIG. 9, elements having the same functions as the elements in the surface plasmon sensor of FIG. 1 bear the same reference numerals as FIG. 1, respectively. The surface plasmon sensor as the seventh embodiment is different from the surface plasmon sensor as the first embodiment in only the wavelength stabilization unit. Therefore, only the differences from the first embodiment are explained below.

The wavelength stabilization unit 50 in the surface plasmon sensor of FIG. 9 comprises a beam splitter 51, a mirror 52, a condenser lens 53, and a reflective fiber grating 54.

The beam splitter 51 is arranged between the collimator lens 20 and the beam expander 21, and partially reflects the laser beam 13 which is emitted from the semiconductor laser unit 14, so as to split off a portion 13R of the laser beam 13 from the optical path toward the prism 10. The mirror 52 reflects the portion 13R of the laser beam 13 which is split off by the beam splitter 51. The condenser lens 53 converges the portion 13R of the laser beam 13 reflected by the mirror 52. The reflective fiber grating 54 is arranged at such a position that the portion 13R of the laser beam 13 reflected by the mirror 52 converges on an end face of the reflective fiber grating 54.

The reflective fiber grating 54 is an optical fiber which contains a core embedded in a cladding, and a plurality of refractive-index varied portions are formed in the core at regular intervals. For example, the reflective fiber grating 54 can be made of an optical fiber for use in communication, and comprises a cladding having an outside diameter of 125 micrometers and a core having a diameter of about 10 micrometers. In the core, the plurality of refractive-index varied portions are formed by generating two-beam interference fringes of excimer laser light in the ultraviolet region so as to change (increase) refractive indexes of a plurality of portions which are exposed to the two-beam interference light. When the core is doped with germanium dioxide, it is considered that the refractive indexes are changed by chemical change of germanium dioxide which is caused by the exposure to the ultraviolet light.

In the wavelength stabilization unit 50, the portion 13R of the laser beam 13 reflected by the mirror 52 and converged by the condenser lens 53 enters the core of the reflective fiber grating 54 from the end face of the reflective fiber grating 54, and propagates through the core. The above plurality of refractive-index varied portions formed in the core realizes a grating arranged along the propagation direction of the portion 13R of the laser beam 13. This grating partially diffracts and reflects only a component of the portion 13R of the laser beam 13 which has a specific wavelength corresponding to the pitch of the grating so as to feed back the reflected component of the portion 13R of the laser beam 13 to the semiconductor laser unit 14. Therefore, the oscillation wavelength of the semiconductor laser unit 14 is locked at the wavelength selected by the reflective fiber grating 54.

Eighth Embodiment

Figure 10:
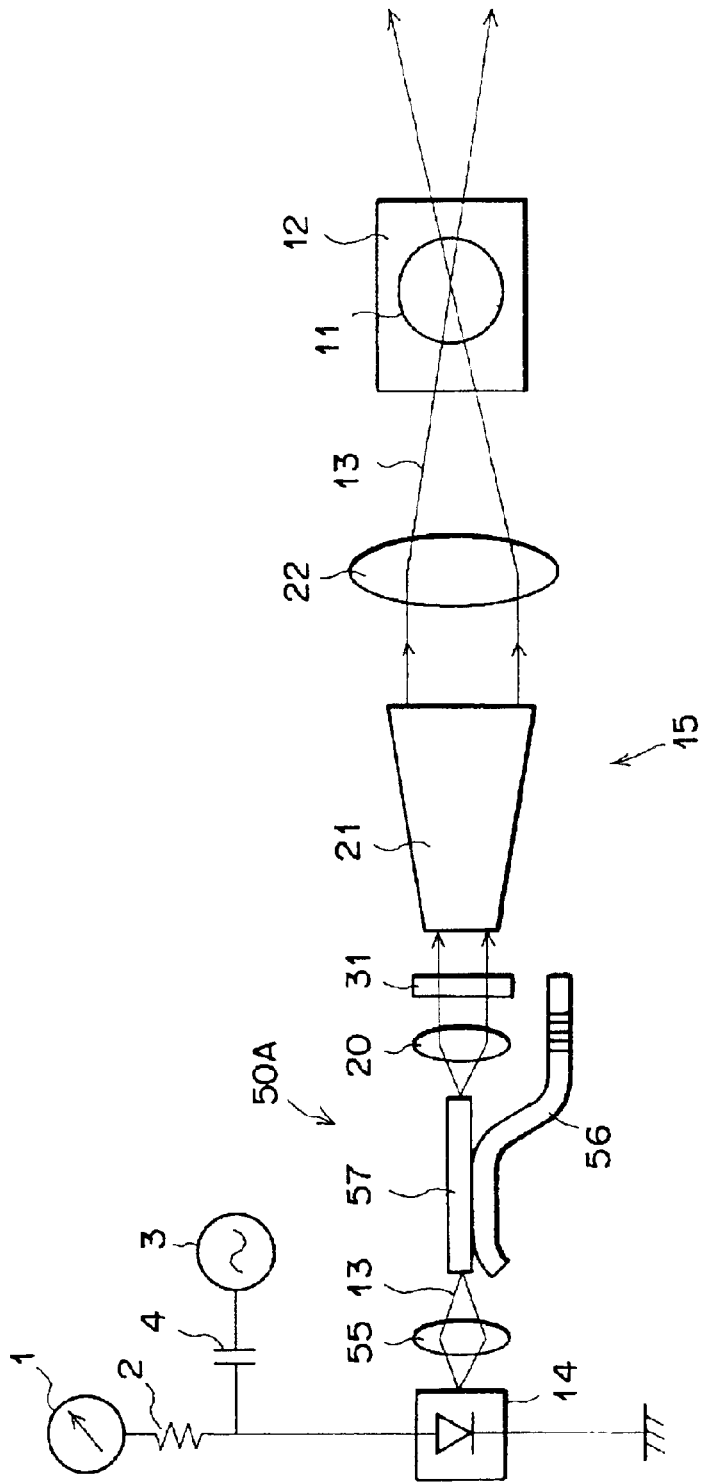
FIG. 10 is a plan view of a surface plasmon sensor as an eighth embodiment of the present invention.

FIG. 10 is a plan view of a surface plasmon sensor as an eighth embodiment of the present invention. In FIG. 10, elements having the same functions as the elements in the surface plasmon sensor of FIG. 4 bear the same reference numerals as FIG. 4, respectively. The surface plasmon sensor as the eighth embodiment is different from the surface plasmon sensor as the second embodiment in only the wavelength stabilization unit. Therefore, only the differences from the second embodiment are explained below.

The wavelength stabilization unit 50A in the surface plasmon sensor of FIG. 10 comprises a condenser lens 55 and first and second optical fibers 56 and 57. The condenser lens 55 converges the laser beam 13 emitted from the semiconductor laser unit 14. The first optical fiber 56 contains a plurality of refractive-index varied portions which are similar to those formed in the reflective fiber grating 54 in the seventh embodiment. The second optical fiber 57 is coupled to the first optical fiber 56 so as to form a fiber coupler.

When the laser beam 13 converged by the condenser lens 55 enters the second optical fiber 57 from an end of the second optical fiber 57, and propagates in the second optical fiber 57, the laser beam 13 is split into two portions. The first portion of the laser beam 13 propagates through the second optical fiber 57, and is output from the other end of the second optical fiber 57 for use in measurement of the specimen 11. The second portion of the laser beam 13 propagates from the second optical fiber 57 to the first optical fiber 56 through the coupling of the first and second optical fibers 56 and 57, and propagates in the first optical fiber 56. Then, a component of the second portion of the laser beam 13 having a specific wavelength is diffracted and reflected by the grating realized by the plurality of refractive-index varied portions. The reflected component of the second portion of the laser beam 13 is fed back to the semiconductor laser unit 14 through the second optical fiber 57 and the condenser lens 55. Therefore, the oscillation wavelength of the semiconductor laser unit 14 is locked at the wavelength selected by the first optical fiber 56.

Ninth Embodiment

Figure 11:
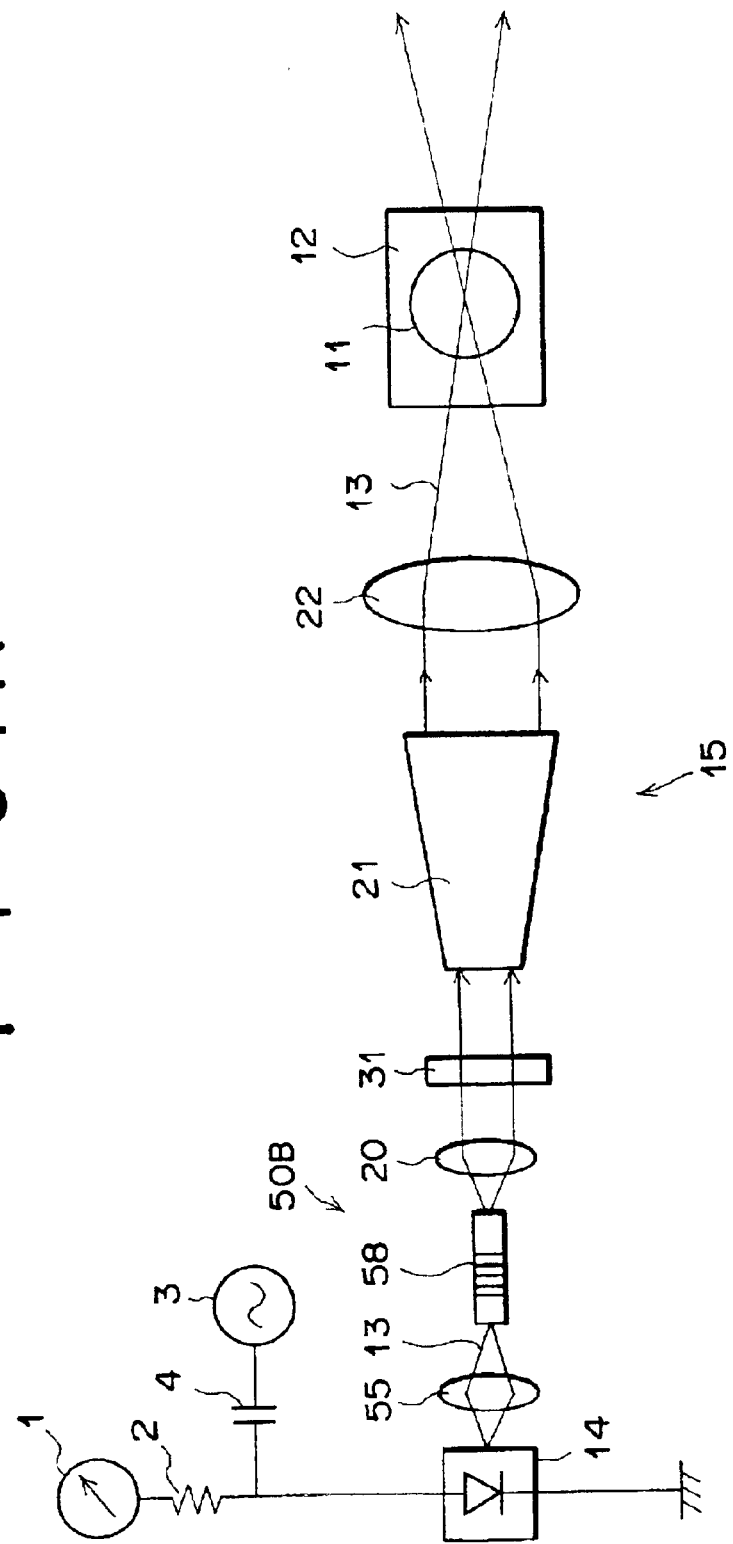
FIG. 11 is a plan view of a surface plasmon sensor as a ninth embodiment of the present invention.

FIG. 11 is a plan view of a surface plasmon sensor as a ninth embodiment of the present invention. In FIG. 11, elements having the same functions as the elements in the surface plasmon sensor of FIG. 10 bear the same reference numerals as FIG. 10, respectively. The surface plasmon sensor as the ninth embodiment is different from the surface plasmon sensor as the eighth embodiment in only the wavelength stabilization unit. Therefore, only the differences from the eighth embodiment are explained below.

The wavelength stabilization unit 50B in the surface plasmon sensor of FIG. 11 comprises a condenser lens 55 and a partially reflective fiber grating 58. The condenser lens 55 converges the laser beam 13 emitted from the semiconductor laser unit 14. The partially reflective fiber grating 58 is arranged at such a position that the laser beam 13 converges on an end face of the partially reflective fiber grating 58.

The partially reflective fiber grating 58 has substantially the same structure as the reflective fiber grating 54 in the surface plasmon sensor of FIG. 9, and partially diffracts and reflects only a portion of the laser beam 13 which has a specific wavelength corresponding to the pitch of the grating so as to feed back the reflected portion of the laser beam 13 to the semiconductor laser unit 14. Therefore, the oscillation wavelength of the semiconductor laser unit 14 is locked at the wavelength selected by the partially reflective fiber grating 58. In addition, the remaining portion of the laser beam 13 propagates through the partially reflective fiber grating 58, and is output from the other end face of the partially reflective fiber grating 58 for use in measurement of the specimen 11.

Tenth Embodiment

Figure 12:
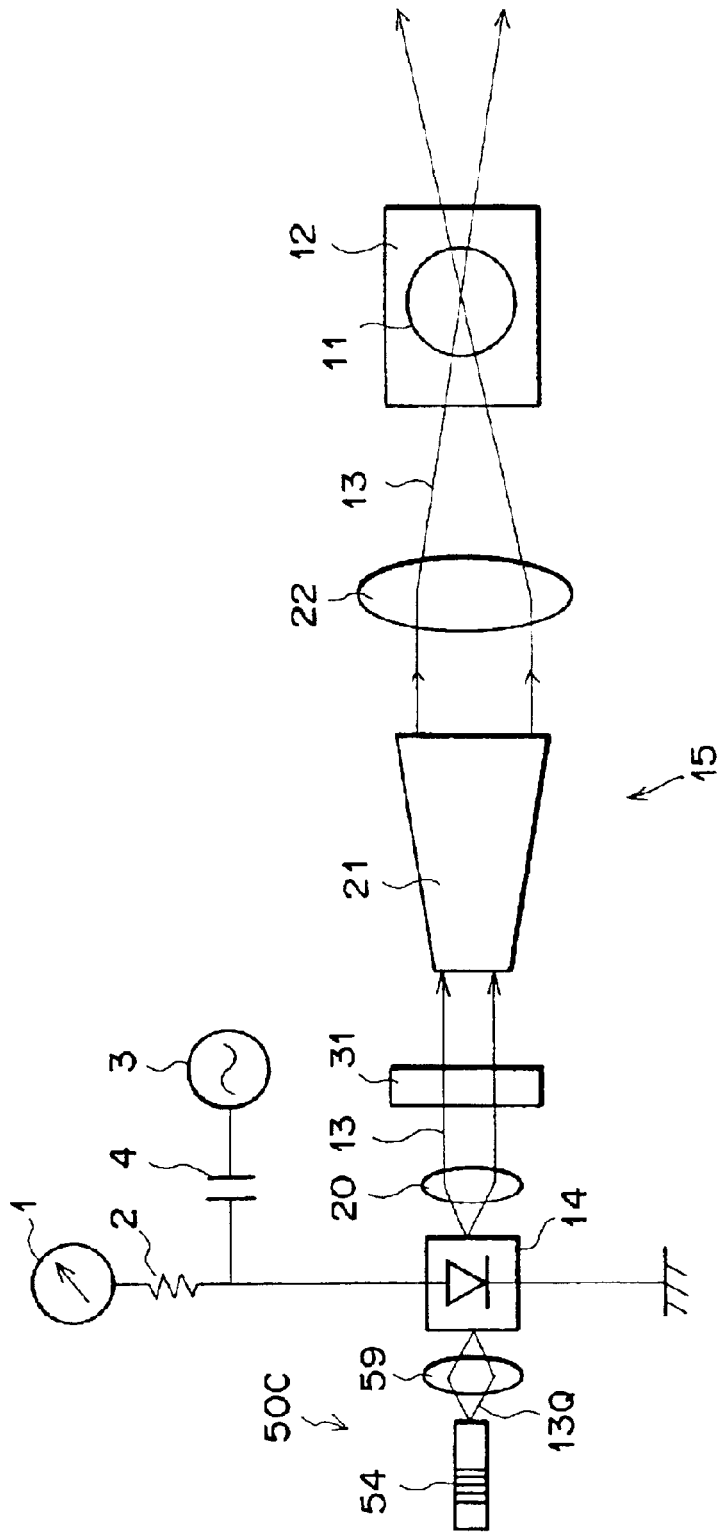
FIG. 12 is a plan view of a surface plasmon sensor as a tenth embodiment of the present invention.

FIG. 12 is a plan view of a surface plasmon sensor as a tenth embodiment of the present invention. In FIG. 12, elements having the same functions as the elements in the surface plasmon sensor of FIG. 11 bear the same reference numerals as FIG. 11, respectively. The surface plasmon sensor as the tenth embodiment is different from the surface plasmon sensor as the ninth embodiment in only the wavelength stabilization unit. Therefore, only the differences from the ninth embodiment are explained below.

The wavelength stabilization unit 50C in the surface plasmon sensor of FIG. 12 comprises a condenser lens 59 and a reflective fiber grating 54. The collimator lens 59 collimates backward emission light 13Q which is emitted from the backward side of the semiconductor laser element 14. The reflective fiber grating 54 is arranged at such a position that the backward emission light 13Q converges on an end face of the reflective fiber grating 54.

The reflective fiber grating 54 partially diffracts and reflects only a portion of the backward emission light 13Q which has a specific wavelength corresponding to the pitch of the grating so as to feed back the reflected portion of the backward emission light 13Q to the semiconductor laser unit 14. Therefore, the oscillation wavelength of the semiconductor laser unit 14 is locked at the wavelength selected by the reflective fiber grating 54.

Eleventh Embodiment

Figure 13:
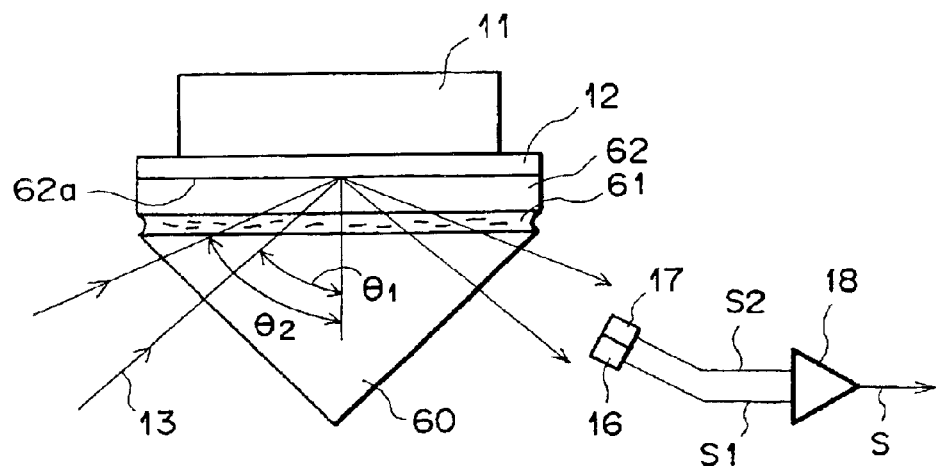
FIG. 13 is a side view of a portion of a surface plasmon sensor as an eleventh embodiment of the present invention.

FIG. 13 is a side view of a portion of a surface plasmon sensor as an eleventh embodiment of the present invention. In FIG. 13, elements having the same functions as the elements in the portion of the surface plasmon sensor illustrated in FIG. 2 bear the same reference numerals as FIG. 2, respectively. The surface plasmon sensor as the eleventh embodiment is basically different from the construction of FIG. 2 in that a dielectric block 62 is formed between a prism 60 and the metal film 12. Therefore, only the differences from the construction of FIG. 2 are explained below.

The dielectric block 62 is made of glass, has a form of approximately a rectangular parallelepiped, and is coupled to the upper face of the prism 60 through an index matching liquid 61 which has the same refractive index as the prism 60 and the dielectric block 62.

The laser beam 13 is injected into the prism 60 so that the laser beam 13 is totally reflected at a boundary 62a between the dielectric block 62 and the metal film 12. Since the dielectric block 62 and the prism 60 are made of the same material, and coupled to each other through the index matching liquid 61 having the same refractive index as the prism 60 and the dielectric block 62, the structure formed with the prism 60, the dielectric block 62, and the index matching liquid 61 is optically identical to a single-piece prism.

Twelfth Embodiment

Figure 14:
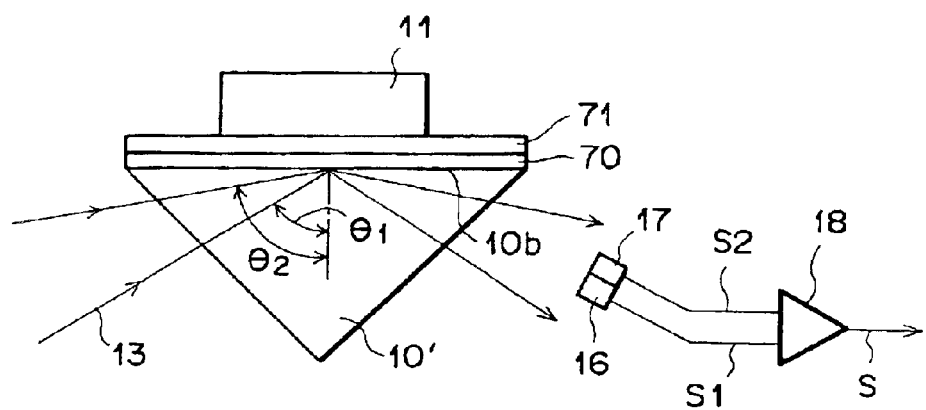
FIG. 14 is a side view of a portion of a leakage mode sensor as a twelfth embodiment of the present invention.

FIG. 14 is a side view of a portion of a leakage mode sensor as a twelfth embodiment of the present invention. In the leakage mode sensor as the twelfth embodiment, a cladding layer 70 is formed on a face (the upper face illustrated in FIG. 14) of a dielectric block 10', and an optical waveguide layer 71 is formed on the cladding layer 70. The other portions of the leakage mode sensor of FIG. 14 are basically identical to the corresponding portions of the surface plasmon sensor as the first embodiment. That is, a high-frequency current RF is superimposed on a driving current of a semiconductor laser unit as a light source, and a means for stabilizing the oscillation wavelength of the semiconductor laser unit is provided. Thus, the same advantages as the first embodiment are obtained.

The dielectric block 10' is made of, for example, a synthetic resin or optical glass such as BK7. The cladding layer 70 is made of a dielectric material having a refractive index lower than the refractive index of the dielectric block 10' or a metal such as gold, and has a form of a thin film. The optical waveguide layer 71 is made of a dielectric material (e.g., PMMA) having a refractive index higher than the refractive index of the cladding layer 70, and has a form of a thin film. For example, the thickness of the cladding layer 70 is about 36.5 nm when the cladding layer 70 is a metal film, and the thickness of the optical waveguide layer 71 is about 700 nm when the optical waveguide layer 71 is made of PMMA.

When the laser beam 13 emitted from a laser light source (not shown in FIG. 14) is injected into the dielectric block 10' so that the laser beam 13 is incident on the cladding layer 70 at an incident angle greater than a critical angle for total reflection, the laser beam 13 is totally reflected from the boundary 10b between the dielectric block 10' and the cladding layer 70. However, when the laser beam 13 which has a specific wave number penetrates the cladding layer 70, and is incident on the optical waveguide layer 71 at a specific incident angle, the laser beam 13 propagates in the optical waveguide layer 71 in a propagation mode, i.e., the propagation mode is excited. When the propagation mode is excited, almost all portions of the incident light can enter the optical waveguide layer 71, and the attenuated total reflection occurs, i.e., the intensity of the light totally reflected from the boundary 10b sharply decreases.

The above specific wave number depends on the refractive index of the specimen 11 placed on the optical waveguide layer 71. Therefore, it is possible to measure the refractive index of the specimen 11 and other properties of the specimen 11 relating to the refractive index of the specimen 11, based on the difference signal S at the above specific incident angle at which the attenuated total reflection occurs.

Additional Matters (a) The present invention can also be applied to other surface plasmon sensors including a semiconductor laser unit as a light source. For example, the present invention can also be applied to: (i) a surface plasmon sensor designed to detect only a specific component by forming on the metal film a layer of a specific binding material which is capable of specific binding to a specimen, e.g., a surface plasmon sensor designed to detect an antigen-antibody reaction; and (ii) a surface plasmon sensor designed to obtain a two-dimensional distribution of a physical property of a specimen which is placed on the metal film.

(b) In each of the first to twelfth embodiments, the semiconductor laser unit and the wavelength stabilization unit realizing the optical feedback are separately provided. Alternatively, it is possible to use as the light source a semiconductor laser unit in which a wavelength stabilization unit is built in, such as a DFB (distributed feedback) laser or DBR (distributed Bragg reflector) laser. Even when the wavelength stabilization unit is built in the semiconductor laser unit, the same advantages are obtained.

(c) In each of the first to twelfth embodiments, the oscillation wavelength of the semiconductor laser unit is stabilized by optical feedback. Alternatively, it is possible to stabilize the oscillation wavelength by electrically and finely controlling the temperature and the driving current of the semiconductor laser unit.

What is claimed is:

1. A sensor comprising:
   a dielectric block;
   a thin film formed on a face of the dielectric block and in contact with a specimen;
   a semiconductor laser unit as a light source which emits a light beam;
   a first optical system which injects the light beam into the dielectric block so that the light beam is incident on a boundary between the dielectric block and the thin film at a plurality of incident angles which are greater than a critical angle for total reflection; and
   a light detecting unit which detects a state of attenuated total reflection by measuring an intensity of the light beam totally reflected from the boundary;
   wherein said semiconductor laser unit is driven with a driving current on which a high frequency component is superimposed.

2. A sensor according to claim 1, wherein said semiconductor laser unit comprises a stabilization unit for stabilizing an oscillation wavelength.

3. A sensor according to claim 2, wherein said stabilization unit comprises, a second optical system which feeds back to the semiconductor laser unit a portion of the light beam emitted from the semiconductor laser unit, and
   a wavelength selection unit which selects a wavelength of the portion of the light beam.

4. A sensor according to claim 3, wherein the frequency of the high-frequency component superimposed on said semiconductor laser is within the range of 200 MHz–1000 MHz.

5. A sensor according to claim 3, wherein said stabilization unit comprises a resonator disposed from an end of the semiconductor laser unit to a reflecting member.

6. A sensor according to claim 5, wherein said resonator is an external resonator.

7. A sensor according to claim 5, wherein said semiconductor laser unit is disposed at a fixed distance from the reflecting member.

8. A sensor comprising:
   a dielectric block;
   a metal film formed on a face of the dielectric block and in contact with a specimen;
   a semiconductor laser unit as a light source which emits a light beam;
   a first optical system which injects the light beam into the dielectric block so that the light beam is incident on a boundary between the dielectric block and the metal film at a plurality of incident angles which are greater than a critical angle for total reflection; and
   a light detecting unit which detects a state of attenuated total reflection due to surface plasmon resonance by measuring an intensity of the light beam totally reflected from the boundary;
   wherein said semiconductor laser unit is driven with a driving current on which a high frequency component is superimposed.

9. A sensor according to claim 8, wherein said semiconductor laser unit comprises a stabilization unit for stabilizing an oscillation wavelength.

10. A sensor according to claim 9, wherein said stabilization unit comprises,
    a second optical system which feeds back to the semiconductor laser unit a portion of the light beam emitted from the semiconductor laser unit, and
    a wavelength selection unit which selects a wavelength of the portion of the light beam.

11. A sensor according to claim 10, wherein the frequency of the high-frequency component superimposed on said semiconductor laser is within the range of 200 MHz–1000 MHz.

12. A sensor comprising:
    a dielectric block;
    a cladding layer formed on a face of the dielectric block;
    an optical waveguide layer formed on the cladding layer and in contact with a specimen;
    a semiconductor laser unit as a light source which emits a light beam;
    a first optical system which injects the light beam into the dielectric block so that the light beam is incident on a boundary between the dielectric block and the cladding layer at a plurality of incident angles which are greater than a critical angle for total reflection; and
    a light detecting unit which detects a state of attenuated total reflection due to excitation of a propagation mode in the optical waveguide layer, by measuring an intensity of the light beam totally reflected from the boundary;
    wherein said semiconductor laser unit is driven with a driving current on which a high frequency component is superimposed.

13. A sensor according to claim 12, wherein said semiconductor laser unit comprises a stabilization unit for stabilizing an oscillation wavelength.

14. A sensor according to claim 13, wherein said stabilization unit comprises, a second optical system which feeds back to the semiconductor laser unit a portion of the light beam emitted from the semiconductor laser unit, and
    a wavelength selection unit which selects a wavelength of the portion of the light beam.

15. A sensor according to claim 14, wherein the frequency of the high-frequency component superimposed on said semiconductor laser is within the range of 200 MHz–1000 MHz.

* * * * *